United States Patent [19]

Mondet et al.

[11] Patent Number: 5,965,116
[45] Date of Patent: Oct. 12, 1999

[54] USE OF ACRYLIC COPOLYMERS IN COSMETICS AND COMPOSITIONS USED

[75] Inventors: Jean Aulnay Sous Mondet, Bois; Bertrand Lion, Livry Gargan, both of France

[73] Assignee: L'Oreal, Paris, France

[21] Appl. No.: 09/029,757

[22] PCT Filed: Jun. 30, 1997

[86] PCT No.: PCT/FR97/01165

§ 371 Date: Apr. 17, 1998

§ 102(e) Date: Apr. 17, 1998

[87] PCT Pub. No.: WO98/00096

PCT Pub. Date: Jan. 8, 1998

[30] Foreign Application Priority Data

Jul. 2, 1996 [FR] France .................................. 96 08220

[51] Int. Cl.$^6$ ........................ A61K 7/075; A61K 47/32; C08F 20/18; C08F 120/18
[52] U.S. Cl. .................... 424/70.16; 514/772.6; 526/318; 526/318.44; 526/328.5
[58] Field of Search ................. 424/401, 70.16, 424/487, 47, 59, 61, 63–64; 526/318.44, 318, 328.5; 514/772.6, 844–45

[56] References Cited

U.S. PATENT DOCUMENTS 4,552,755 11/1985 Randen .
5,116,924 5/1992 Bung et al. .

OTHER PUBLICATIONS

T. Shohei et al., "Hair Cosmetic", Patent Abstract of Japan for JP 08 092046, (Abstract Only), 96 (8), Aug. 30, 1996.

*Primary Examiner*—Edward J. Webman
*Attorney, Agent, or Firm*—Finnegan, Henderson, Farabow, Garrett & Dunner, L.L.P.

[57] ABSTRACT

The subject of the present invention is the use, in, and for the preparation of, cosmetic or dermatological compositions, of a copolymer which can be obtained by copolymerization of a monomer mixture comprising:

(a) from 5 to 25% by weight of at least one monomer (A) with ethylenic unsaturation containing at least one carboxylic acid function;

(b) from 3 to 30% by weight of at least one monomer (B) of formula (I):

$$H_2C=C(R_1)-COOR_2 \qquad (I)$$

in which $R_1$ denotes a hydrogen atom or a methyl radical, $R_2$ denotes a saturated or unsaturated, linear or branched or cyclic alkyl radical or an aromatic radical, having from 8 to 40 carbon atoms, (c) at least one monomer (C) chosen from the group consisting of tert-butyl methacrylate, tert-butyl acrylate and mixtures thereof, in a proportion greater than 50%, such that the glass transition (Tg) of the polymer is greater than or equal to 15° C., the weight percentages being calculated relative to the total amount of monomers used, as well as to the cosmetic or dermatological compositions used.

23 Claims, No Drawings

USE OF ACRYLIC COPOLYMERS IN COSMETICS AND COMPOSITIONS USED

The present invention relates to the use of acrylic copolymers in, and for the preparation of, cosmetic or dermatological compositions, as well as to the compositions used.

For many cosmetic applications, in particular those intended for the treatment and care of the hair, the skin or the eyelashes, polymers are used which are capable, after application to the support to be treated and drying, of forming a deposit having mechanical properties and adhesive properties. In this respect, polymers are sought which can be removed easily under the action of an aqueous solution of surfactants. In parallel, it is sought to obtain a film-forming deposit which is resistant to environmental moisture, in particular a deposit which does not feel hygroscopic, a rain-resistant deposit (for hair or skin use) or a deposit which is resistant to lachrymal fluid (mascaras). Moreover, a film-forming deposit is sought to provide cosmetic properties such as the soft feel generally imparted by hydrophobic substances in cosmetics.

Another problem relating to deposit polymers occurs in the field of hair care, in particular in the context of products for fixing the hair or for retaining its shape. The reason for this is that it is often difficult to adapt the properties of the polymer which needs to be deposited in order to obtain, at the same time, good fixing of the hair, good staying power of this fixing and easy removal by combing or brushing.

It is known to use acrylic copolymers in cosmetic compositions. By way of example, patent application JP-A-87-167 307 describes a styling polymer obtained by copolymerization of the monomer mixture comprising:
  (i) from 10 to 50% by weight of unsaturated carboxylic acids,
  (ii) from 10 to 70% by weight of acrylic acid esters and/or of methacrylic acid esters,
  (iii) from 0 to 50% of vinyl monomers.

This polymer makes it possible to give the hair good slippery properties while at the same time maintaining a good feel. However, the presence of a fatty chain in the polymer, introduced by the acrylic acid esters and/or the methacrylic acid esters, makes it difficult to remove the polymer once fixed on the hair.

A cosmetic hair composition is also known from application JP-A-08092046, this composition containing a copolymer comprising from 6 to 35% by weight of (meth)acrylic acid or of itaconic acid, from 15 to 50% by weight of $C_{10}$–$C_{18}$-alkyl (meth)acrylate, from 15 to 50% by weight of $C_4$–$C_8$-alkyl (meth)acrylate and from 0 to 25% of vinyl-type monomer, in particular acrylamide-type monomer. However, these polymers are difficult to use in compositions comprising an alcoholic medium, but such compositions are particularly advantageous owing to their fast drying time.

One of the objects of the present invention is thus to use, in cosmetic or dermatological compositions, acrylic polymers having film-forming properties and adhesive and mechanical properties that are satisfactory, these polymers being easily removed under the action of an aqueous solution of surfactants, and being easily incorporated into compositions comprising at least one alcoholic medium. In addition, it is an object of the invention to use film-forming polymers which provide good cosmetic properties before and after removal of the composition.

Another object of the invention is to use, in and for the preparation of hairstyling compositions, polymers having both high-performance fixing properties which offer good resistance to weak mechanical stresses and good rigidity, but are then readily removed by shampooing, brushing or combing, while at the same time providing good cosmetic properties such as a soft feel. In particular, one of the objects of the invention is to propose the use of polymers which are easy to use in hair compositions comprising an alcoholic medium in order to allow rapid drying of the composition, the said composition having good lacquering power and no sensation of stickiness.

The Applicant has discovered, surprisingly, that these objects can be achieved by using certain particular acrylic copolymers in, and for the preparation of, cosmetic or dermatological compositions.

The subject of the present invention is the use, in, and for the preparation of, cosmetic or dermatological compositions, of a copolymer which can be obtained by copolymerization of a monomer mixture comprising:

(a) from 5 to 25% by weight of at least one monomer (A) with ethylenic unsaturation containing at least one carboxylic acid function;

(b) from 3 to 30% by weight of at least one monomer (B) of formula (I):

$$H_2C=C(R_1)\text{—}COOR_2 \qquad (I)$$

in which
  $R_1$ denotes a hydrogen atom or a methyl radical,
  $R_2$ denotes a saturated or unsaturated, linear or branched or cyclic alkyl radical or an aromatic radical, having from 8 to 40 carbon atoms, (c) at least one monomer (C) chosen from the group consisting of tert-butyl methacrylate, tert-butyl acrylate and mixtures thereof, in a proportion at least greater than 50% by weight, such that the glass transition (Tg) of the polymer is greater than or equal to 15° C., the weight percentages being calculated relative to the total amount of monomers used.

The present invention also relates to cosmetic or dermatological compositions containing, in a cosmetically or dermatologically acceptable medium, at least one copolymer obtained by copolymerization:

(a) of 5 to 25% by weight of at least one monomer (A) with ethylenic unsaturation containing at least one carboxylic acid function;

(b) of 3 to 30% by weight of at least one monomer (B). of formula (I):

$$H_2C=C(R_1)\text{—}COOR_2 \qquad (I)$$

in which
  $R_1$ denotes a hydrogen atom or a methyl radical,
  $R_2$ denotes a saturated or unsaturated, linear or branched or cyclic alkyl radical or an aromatic radical, having from 8 to 40 carbon atoms, (c) of at least one monomer (C) chosen from the group consisting of tert-butyl methacrylate, tert-butyl acrylate and mixtures thereof, in a proportion at least greater than 50% by weight, such that the glass transition (Tg) of the polymer is greater than or equal to 15° C., the weight percentages being calculated relative to the total amount of monomers used.

It has been observed that the copolymer used according to the invention for hair compositions allows very good cosmetic properties to be obtained, in particular a good feel and good removal, both by brushing and by shampooing. In particular, after the composition has been applied, the hair has a pleasant feel without giving a "cardboard" effect, that is to say without making the hair excessively rigid. Thus, the composition has good lacquering power and, after it has been applied to the hair, the film formed is hardly sticky at all. In addition, the copolymer according to the invention shows good compatibility with alcoholic media and can thus be used readily in a composition with a fast drying time.

Other objects will become apparent on reading the description and the examples which follow.

Preferably:
the content of monomer (A) ranges from 6 to 20% by weight, and better still from 6 to 15% by weight,
the content of monomer (B) ranges from 5 to 25% by weight, and better still from 13 to 22% by weight,
the content of monomer (C) ranges from 55 to 80% by weight, and better still from 60 to 70% by weight.

The monomers (A) used to prepare the polymers according to the invention are chosen, for example, from the group consisting of: monocarboxylic acids with ethylenic unsaturation, such as acrylic acid, methacrylic acid and crotonic acid; dicarboxylic acids with ethylenic unsaturation, such as maleic acid, fumaric acid and itaconic acid and their monoester or monoamide derivatives with a $C_1$–$C_4$-alkyl group; and allyloxyacetic acid. Acrylic acid, methacrylic acid or a mixture thereof is more particularly used.

In the monomers (B), $R_2$ is preferably a linear or branched saturated alkyl radical having from 8 to 40 carbon atoms, and preferably from 8 to 30 carbon atoms. It may be, in particular, a radical corresponding to the Guerbet alcohols corresponding to the formula —$CH_2$—$CH(R_3)$ $(R_4)$ in which $R_3$ and $R_4$, which may be identical or different, denote a linear or branched, saturated alkyl radical, the total number of carbon atoms in $R_3$ and $R_4$ ranging from 6 to 38, and preferably from 6 to 28.

Advantageously, $R_2$ is chosen from the group formed by lauryl, stearyl and 2-ethylhexyl radicals.

Preferably, the copolymers used according to the invention consist of a mixture of monomers (A), (B) and (C) as defined above.

The copolymers according to the invention preferably have an average molecular weight, measured at the peak height by steric exclusion chromatography, ranging from 5,000 to 2,000,000, and in particular from 20,000 to 1,000,000.

Advantageously, the polymer according to the invention has a glass transition temperature ranging from 40° C. to 90° C.

The copolymer according to the invention can be obtained by radical polymerization of the monomers as defined above.

The radical polymerization can be carried out in solution in a solvent which is common to all the monomers employed and to the polymer obtained, or in a mixture of common solvents. As solvent, mention may be made of ethyl acetate or ethanol. The reaction is generally carried out at a temperature ranging from 30° C. to the boiling point of the solvent employed. The polymerization can also be carried out in a heterogeneous medium, in particular in suspension, by precipitation or by emulsion.

The radical polymerization can be initiated by a conventional organic initiator, for example azobis-N-butyronitrile, bis(2-ethylhexyl) peroxydicarbonate or tert-butyl 2-peroxyethylhexanoate.

When the polymerization is carried out in emulsion, a water-soluble thermal initiator can also be used, such as potassium persulphate, aqueous hydrogen peroxide solution or a water-soluble redox system, for example one of persulphate/metabisulphite type. Moreover, the emulsion is stabilized in a known manner with a surfactant or a mixture of surfactants, those most commonly used being sodium lauryl sulphate and alkyl ethoxysulphates.

The duration of the polymerization reaction can range in general from 4 hours to 18 hours.

Advantageously, the copolymer according to the invention can be partially or totally neutralized depending on the desired solubility of the polymer in the composition. The degree of neutralization can range in particular from 30% to 100%. The neutralization can be carried out using an organic or inorganic base.

As inorganic base, mention may be made of sodium hydroxide or potassium hydroxide. As organic base, mention may be made of an amino alcohol taken from the group consisting of 2-amino-2-methyl-1-propanol (AMP), triethanolamine, triisopropanolamine ((TIPA), monoethanolamine, diethanolamine, tris[1-(2-hydroxy) propyl] amine, 2-amino-2-methyl-1,3-propanediol (AMPD) and 2-amino-2-hydroxymethyl-1,3-propanediol.

The compositions according to the invention can also optionally contain a plasticizer in order to enhance the mechanical properties, the cosmetic properties and the adhesion to keratin substances of the deposited film-forming acrylic polymer after application and drying. The presence of a plasticizer is not obligatory in order to adjust the lacquering power in the lacquer formulations of the invention, in contrast with conventional lacquer formulations.

Of the plasticizers which can be used according to the invention, mention may be made of:
Carbitols from the company Union Carbide, namely Carbitol or diethylene glycol ethyl ether, methyl Carbitol or diethylene glycol methyl ether, butyl Carbitol or diethylene glycol butyl ether or hexyl Carbitol or diethylene glycol hexyl ether,
the Cellosolves from the company Union Carbide, namely Cellosolve or ethylene glycol ethyl ether, butyl Cellosolve or ethylene glycol butyl ether, and hexyl Cellosolve or ethylene glycol hexyl ether,
propylene glycol derivatives and in particular propylene glycol phenyl ether, propylene glycol diacetate, dipropylene glycol butyl ether, tripropylene glycol butyl ether and the Dowanols from the company Dow Chemical, namely Dowanol PM or propylene glycol methyl ether, Dowanol DPM or dipropylene glycol methyl ether and Dowanol TPM or tripropylene glycol methyl ether.

Mention may also be made of:
diethylene glycol methyl ether or Dowanol DM from the company Dow Chemical,
castor oil oxyethylenated with 40 mol of ethylene oxide, such as that sold by the company Rhône Poulenc under the name "Mulgofen LE-719",
benzyl alcohol,
triethyl citrate sold by the company Pfizer under the name 1,3-butylene glycol,
diethyl, dibutyl and diisopropyl phthalates and adipates,
diethyl and dibutyl tartrates,
diethyl, dibutyl and bis(2-ethylhexyl) phosphates, and
glycerol esters such as glyceryl diacetate (diacetin) and glyceryl triacetate (triacetin).

The plasticizers are chosen more particularly from those which are hydrophilic or water-soluble.

The plasticizer is present in a proportion preferably ranging from 0 to 20% by weight relative to the weight of the film-forming polymer. This proportion varies according to the application envisaged.

The cosmetic and dermatological compositions according to the invention thus contain, in a cosmetically or dermatologically acceptable support, the polymers as described above, for applications as varied as those encountered, for example, in the field of haircare, make-up or skincare, or any other cosmetic field in which it is desirable or sought to use a film-forming substance.

The copolymers according to the invention can be used alone as film-forming agents or alternatively as additives to conventional film-forming agents in, and for the preparation of, cosmetic or dermatological compositions.

Among the applications preferably envisaged by the present invention, mention may be made more particularly of:

the field of hair products (hair beauty, care or washing), in which the compositions according to the invention can be in the form of aerosols, foam, shampoos, conditioners, styling or treating lotions or gels, or shaping, setting or fixing lacquers or lotions.

the field of make-up products, in particular products for making up the nails, the eyelashes or the lips, in which the compositions according to the invention can be in the form of nail varnish; mascaras or eyeliners; lipsticks.

the field of skincare products (antisun products, sera, masks, lotions, milks, creams).

The copolymer is present in the cosmetic or dermatological compositions of the invention at a concentration generally ranging from 0.1 to 50%, and more preferably from 1 to 30%, by weight relative to the total weight of the composition. It varies depending on the cosmetic or dermatological application envisaged.

In the case of hair compositions, the polymer concentration can range from 0.5 to 25%, and in particular from 1 to 20%, by weight relative to the total weight of the composition.

In the case of nail varnishes, this proportion generally ranges from 2 to 35% by weight, and when the copolymer of the invention is used alone as film-forming agent, the concentration is equal to or greater than 30% by weight relative to the total weight of the composition.

In the case of mascaras or eyeliners, the polymer concentration generally ranges from 1 to 30% by weight relative to the total weight of the composition.

In the case of skincare compositions, the polymer concentration ranges from 0.5 to 20% by weight relative to the total weight of the composition.

The cosmetically acceptable support for the compositions according to the invention preferably consists of water, or one or more cosmetically acceptable organic solvents, or a mixture of water and one or more cosmetically acceptable organic solvents.

Among these organic solvents, $C_1$–$C_4$ lower alcohols such as ethanol are more particularly used.

The copolymers according to the invention are dissolved or dispersed in the support for the compositions of the invention.

The compositions can also, of course, contain various adjuvants intended to make them acceptable in a particular cosmetic application.

The compositions according to the invention can contain conventional cosmetic additives chosen from fatty substances such as mineral, plant, animal or synthetic oils, animal, fossil, plant, mineral or synthetic waxes, organic solvents, thickeners, softeners, antifoaming agents, moisturizers, wetting agents, treating agents (agents for combating hair loss, antidandruff agents, etc.), antiperspirants, basifying agents, UV-A or UV-B or broadband sunscreens, dyes, pigments, fragrances, plasticizers, preserving agents, anionic, nonionic or amphoteric organic polymers which are compatible with the copolymers of the invention, and propellants when the compositions are in aerosol form.

Needless to say, a person skilled in the art will take care to select the optional additional compound(s) mentioned above such that the advantageous properties intrinsically associated with the compositions according to the invention are not, or are not substantially, adversely affected by the addition(s) envisaged.

The subject of the invention is also a process for the cosmetic treatment of keratin substances such as the skin, the hair, the scalp, the eyelashes, the eyebrows, the nails or the lips, characterized in that it consists in applying a composition as defined above to these.

The examples which follow serve to illustrate the invention without, however, being limiting in nature.

PREPARATION EXAMPLES 1 TO 5

Example 1

Preparation of a Copolymer Obtained from a Mixture Consisting of:

15% by weight of acrylic acid

65% by weight of tert-butyl acrylate

20% by weight of lauryl acrylate 15 g of acrylic acid, 65 g of tert-butyl acrylate and 20 g of lauryl acrylate were introduced successively into a reactor under a stream of nitrogen. 200 g of ethyl acetate and 2 ml of tert-butyl peroxy-2-ethylhexanoate, sold under the name "Trigonox 21 S" by the company Akzo, were then added. The mixture was stirred at room temperature in order to obtain a homogeneous medium. It was then heated to the reflux point of the ethyl acetate in order to carry out the polymerization for 12 hours. The reaction medium was then diluted by adding 100 g of ethyl acetate and was then cooled to room temperature.

The reaction solution was purified by precipitation from 8 litres of petroleum ether. The precipitated polymer obtained was dried in an oven. 91 g of polymer having the following characteristics were obtained:

Acid number: 137.5

Tg=44° C.

The characterization of the molecular weight was carried out by steric exclusion chromatography on a microstyragel column eluted with tetrahydrofuran. The results are expressed relative to a polystyrene standard.

The polymer obtained gives a main peak corresponding to a molecular weight of 322,000 and a shoulder towards high molecular weights corresponding to a molecular weight of 1,308,000.

Example 2

Preparation of a Copolymer Obtained from a Mixture Consisting of:

15% by weight of acrylic acid

70% by weight of tert-butyl acrylate

15% by weight of stearyl methacrylate

The polymer was prepared according to the same operating conditions as in Example 1. 90 g of polymer having the following characteristics were obtained:

Acid number: 130

Tg=53° C.

Molecular weight: main peak: MW=182,000
 shoulder: 1,030,000

Example 3

Preparation of a Copolymer Obtained from a Mixture Consisting of:

15% by weight of acrylic acid

70% by weight of tert-butyl acrylate

15% by weight of stearyl acrylate

The polymer was prepared according to the same operating conditions as in Example 1. 90 g of polymer having the following characteristics were obtained:

Acid number: 129

Tg52° C.

Molecular weight: main peak: MW=160,000; no shoulder

Example 4

Preparation of a Copolymer Obtained from a Mixture Consisting of:

15% by weight of acrylic acid

65% by weight of tert-butyl acrylate

20% by weight of lauryl acrylate

The polymer was prepared according to the same operating conditions as in Example 1, replacing the ethyl acetate with ethanol. 80 g of polymer having the following characteristics were obtained:

Acid number: 139.5

Tg=44° C.

Molecular weight: main peak: MW=96,000; no shoulder

Example 5

Preparation of a Copolymer Obtained from a Mixture Consisting of:

20% by weight of acrylic acid

60% by weight of tert-butyl acrylate

20% by weight of 2-ethylhexyl acrylate

The polymer was prepared according to the same operating conditions as in Example 4, using only 1 ml of initiator. 80 g of polymer having the following characteristics were obtained:

Acid number: 161

Molecular weight: main peak: MW=113,000; no shoulder

COMPOSITION EXAMPLES 6 TO 12

Example 6

Aerosol Styling Lacquer

| Composition A | | |
| --- | --- | --- |
| Copolymer of Example 1 | | 2 g |
| 2-Amino-2-methyl-1-propanol for 100% neutralization | qs | |
| Ethanol | qs | 100 g |

An aerosol hair lacquer was prepared by packaging the following in a suitable aerosol container:

| Composition A | 65 g |
| --- | --- |
| Dimethyl ether | 35 g |

The valve was fixed on and the container sealed hermetically. When applied to the hair, the lacquer has good lacquering power and good staying power. The polymer film is easily removed by brushing. The hair feels attractive, even after brushing.

Example 7

Aerosol Styling Lacquer

| Composition B | | |
| --- | --- | --- |
| Copolymer of Example 2 | | 2 g |
| 2-Amino-2-methyl-1-propanol for 100% neutralization | qs | |
| Ethanol | qs | 100 g |

An aerosol hair lacquer was prepared by packaging the following in a suitable aerosol container:

| Composition B | 65 g |
| --- | --- |
| Dimethyl ether | 35 g |

The valve was fixed on and the container sealed hermetically. When applied to the hair, the lacquer has good lacquering power and good staying power. The polymer film is easily removed by brushing. The hair feels attractive, even after brushing.

Example 8

Aerosol Styling Lacquer

| Composition C | | |
| --- | --- | --- |
| Copolymer of Example 3 | | 2 g |
| 2-Amino-2-methyl-1-propanol for 100% neutralization | qs | |
| Ethanol | qs | 100 g |

An aerosol hair lacquer was prepared by packaging the following in a suitable aerosol container:

| Composition C | 65 g |
| --- | --- |
| Dimethyl ether | 35 g |

The valve was fixed on and the container sealed hermetically. When applied to the hair, the lacquer has good lacquering power and good staying power. The polymer film is easily removed by brushing. The hair feels attractive, even after brushing.

Example 9

Aerosol Styling Lacquer

| Composition D | | |
| --- | --- | --- |
| Copolymer of Example 5 | | 8.6 g |
| 2-Amino-2-methyl-1-propanol for | qs | |

-continued

| Composition D | | |
|---|---|---|
| 50% neutralization | | |
| Ethanol | qs | 100 g |

An aerosol hair lacquer was prepared by packaging the following in a suitable aerosol container:

| | | |
|---|---|---|
| Composition D | 37 g | |
| Dimethyl ether | 43 g | |
| Pentane | 20 g | |

The valve was fixed on and the container sealed hermetically. When applied to the hair, the lacquer has good lacquering power and good staying power, without cosmetic defects such as powdering or stickiness. The polymer film is easily removed by brushing. The hair feels attractive, even after brushing.

Example 10
Aerosol Styling Lacquer

| Composition E | | |
|---|---|---|
| Copolymer of Example 4 | | 8.6 g |
| 2-Amino-2-methyl-1-propanol for | qs | |
| 50% neutralization | | |
| Ethanol | qs | 100 g |

An aerosol hair lacquer was prepared by packaging the following in a suitable aerosol container:

| | | |
|---|---|---|
| Composition E | 37 g | |
| Dimethyl ether | 43 g | |
| Pentane | 20 g | |

The valve is fixed on and the container sealed hermetically. When applied to the hair, the lacquer has good lacquering power and good staying power, without cosmetic defects such as powdering or stickiness. The polymer film is easily removed by brushing. The hair feels attractive, even after brushing.

Example 11
Mascara
1) Preparation of an Aqueous Dispersion of the Polymer of Example 4:

30g of the polymer of Example 4 are added to a solution of 90 g of methyl ethyl ketone and 1.76 g of 2-amino-2-methyl-1-propanol (the amount corresponding to 30% neutralization according to the acid number). After stirring at room temperature for 30 minutes, the polymer has completely dissolved.

An aqueous phase is stirred into the organic phase thus obtained using an Ultra-Turrax type stirrer at 2000 rev/min in order to prepare the emulsion, this emulsion consisting of 120 g of deionized water. After addition of the aqueous phase is complete, at room temperature, stirring is continued for 10 to 15 min, which allows a translucent, stable emulsion to be obtained.

Concentration is then carried out using a rotary evaporator under partial vacuum at a temperature below 50° C. After removal of the methyl ethyl ketone, a stable dispersion whose polymer concentration is 20% by weight relative to the total weight of the composition is obtained.

The particle size is measured by quasi-elastic light scattering using a model M4 Coulter, and gives the following results:

Particle size: 45 nm.
Size polydispersity: 0.26
2) Preparation of the Mascara:

| Part A | | |
|---|---|---|
| Triethanolamine stearate | | 12 g |
| Beeswax | | 6 g |
| Carnauba wax | | 1 g |
| Paraffin | | 3.5 g |
| Part B | | |
| Iron oxides | | 6 g |
| Part C | | |
| Hydroxyethylcellulose | | 1 g |
| ("Cellosize QP" from Amerchol) | | |
| Gum arabic | | 2 g |
| Keratin hydrolysate | | 1.8 g |
| Part D | | |
| Aqueous dispersion of the polymer of Example 4 | | 5 g |
| Preserving agents | qs | |
| Water | qs | 100 g |

This mascara is obtained by heating the ingredients of Part A at 85° C., to which is added Part B, and the mixture is stirred using a turbomixer. The water in the preparation is then boiled and the preserving agents added, followed, at 85° C., by the ingredients of Part C. The aqueous phase obtained is then added to Part A with stirring using a turbomixer, after which the aqueous dispersion of polymer of Part D is added and the mixture is paddle-stirred.

Example 12
Nailcare
A care base for the nails having the following composition is prepared:

| | |
|---|---|
| Aqueous dispersion of the polymer of Example 4 (prepared according to Example 11.1) | 82.3 g |
| Water | 15 g |
| Glycerol | 2 g |
| Formaldehyde | 0.5 g |
| Hydroxypropylcellulose | 0.2 g |

The aqueous dispersion, the glycerol and the formaldehyde are mixed together, followed by gentle stirring, and the hydroxypropylcellulose is then dispersed in the solution obtained.

This composition applies easily to the nails and allows a shiny film to be obtained which is easily removed with water. Daily application of this composition to the nails for several weeks hardens the nails.

We claim:
1. A cosmetic and/or dermatological composition comprising, in a cosmetically and/or dermatologically acceptable medium, at least one copolymer formed from the following monomer mixture:
(i) from 5 to 25% by weight of at least one monomer (A) with ethylenic unsaturation containing at least one carboxylic acid function;
(ii) from 3 to 30% by weight of at least one monomer (B) of formula (I):

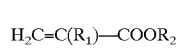  (I)

in which:

R₁ denotes a hydrogen atom or a methyl radical, and

R₂ denotes a saturated or unsaturated, linear or branched or cyclic alkyl radical or an aromatic radical having from 8 to 40 carbon atoms; and (c) more than at least 50% by weight of at least one monomer (C) selected from tert-butyl methacrylate and tert-butyl acrylate, wherein the glass transition (Tg) of said at least one copolymer is at least 15° C., and further wherein said percentages of monomers (A), (B), and (C) are calculated relative to the total amount of monomers used to form said at least one copolymer.

2. A cosmetic and/or dermatological composition according to claim 1, wherein said amount of said at least one monomer (A) ranges from 6 to 20% by weight, said at least one monomer (B) ranges from 5 to 25% by weight, and said at least one monomer (C) ranges from 55 to 80% by weight, relative to the total weight of monomers used to form said at least one copolymer.

3. A cosmetic and/or dermatological composition according to claim 2, wherein said at least one monomer (A) ranges from 6 to 15% by weight, said at least one monomer (B) ranges from 13 to 22% by weight, and said at least one monomer (C) ranges from 60 to 70% by weight, relative to the total weight of monomers used to form said at least one copolymer.

4. A cosmetic and/or dermatological composition according to claim 1, wherein said at least one monomer (A) is selected from monocarbooxylic acids with ethylenic unsaturation; dicarboxylic acids with ethylenic unsaturation and the monoester and monoamide derivatives thereof with a $C_1$–$C_4$ alkyl group; and allyloxyacetic acid.

5. A cosmetic and/or dermatological composition according to claim 1, wherein said at least one monomer (A) is selected from acrylic acid and methacrylic acid.

6. A cosmetic and/or dermatological composition according to claim 1, wherein, in said at least one monomer (B), R₂ is a linear or branched saturated alkyl radical having from 8 to 40 carbon atoms.

7. A cosmetic and/or dermatological composition according to claim 6, wherein R₂ is a linear or branched saturated alkyl radical having from 8 to 30 carbon atoms.

8. A cosmetic and/or dermatological composition according to claim 6, wherein, in said at least one monomer (B), R₂ is selected from lauryl, stearyl and 2-ethylhexyl radicals.

9. A cosmetic and/or dermatological composition according to claim 1, wherein said at least one copolymer has an average molecular weight, measured at the peak height by steric exclusion chromatography, ranging from 5,000 to 2,000,000.

10. A cosmetic and/or dermatological composition according to claim 9, wherein said at least one copolymer has an average molecular weight, measured at the peak height by steric exclusion chromatography, ranging from 20,000 to 1,000,000.

11. A cosmetic and/or dermatological composition according to claim 1, wherein said glass transition (Tg) ranges from 40° C. to 90° C.

12. A cosmetic and/or dermatological composition according to claim 1, wherein said at least one copolymer is present in an amount ranging from 0.1 to 50% by weight relative to the total weight of said composition.

13. A cosmetic and/or dermatological composition according to claim 12, wherein said at least one copolymer is present in an amount ranging from 1 to 30% by weight, relative to the total weight of said composition.

14. A cosmetic and/or dermatological composition according to claim 1, wherein said at least one copolymer is neutralized to a degree ranging from 30 to 100%.

15. A cosmetic and/or dermatological composition according to claim 1, wherein said cosmetically and/or dermatologically acceptable medium comprises water, at least one cosmetically or dermatologically acceptable organic solvent, or a mixture thereof.

16. A cosmetic and/or dermatological composition according to claim 15, wherein said at least one cosmetically or dermatologically acceptable organic solvent is selected from $C_1$–$C_4$ lower alcohols.

17. A cosmetic and/or dermatological composition according to claim 1, wherein said at least one copolymer is dissolved or dispersed in said cosmetically and/or dermatologically acceptable medium.

18. A cosmetic and/or dermatological composition according to claim 1, wherein said composition further comprises at least one plasticizer.

19. A cosmetic and/or dermatological composition according to claim 1, wherein said composition further comprises at least one conventional cosmetic additive selected from fatty substances; organic solvents; thickeners; softeners; antifoaming agents; moisturizers; wetting agents; treating agents; antiperspirants; basifying agents; UV-A and UV-B broad-band sunscreens; dyes; pigments; fragrances; preserving agents; anionic, nonionic and amphoteric organic polymers which are compatible with said at least one copolymer; and propellants.

20. A cosmetic and/or dermatological composition according to claim 19, wherein said fatty substances are selected from plant, animal, mineral and synthetic oils and animal, fossil, plant, mineral or synthetic waxes.

21. A cosmetic and/or dermatological composition according to claim 1, wherein said composition is a hair composition, a make-up composition, or a skin care composition.

22. A method of preparing a cosmetic and/or dermatological composition comprising including in said composition at least one copolymer according to claim 1 as a film-forming agent or as an additive of a film-forming agent.

23. A method for cosmetically treating a keratin substance comprising applying an effective amount of a composition according to claim 1 to said keratin substance.

* * * * *

UNITED STATES PATENT AND TRADEMARK OFFICE
CERTIFICATE OF CORRECTION

PATENT NO. : 5,965,116
DATED : October 12, 1999
INVENTOR(S) : Jean A. S. Mondet, et al.

It is certified that error appears in the above-identified patent and that said Letters Patent is hereby corrected as shown below:

Title page, item [75], "Inventors: Jean Aulnay Sous Mondet, Bois"; should read -- Inventors: Jean Mondet, Aulnay sous Bois --.

Signed and Sealed this

Sixteenth Day of May, 2000

Attest:

Q. TODD DICKINSON

*Attesting Officer*      *Director of Patents and Trademarks*